United States Patent [19]
Ritter et al.

[11] Patent Number: 5,648,518
[45] Date of Patent: *Jul. 15, 1997

[54] PROCESS FOR PRODUCING ESTERS OF (METH) ACRYLIC ACID AND POLYHYDRIC ALCOHOLS

[75] Inventors: Wolfgang Ritter, Haan; Hans-Dieter Sitz, Rommerskirchen; Ludwig Speitkamp, Duesseldorf, all of Germany

[73] Assignee: Henkel Kommanditgesellschaft auf Aktien, Duesseldorf, Germany

[*] Notice: The portion of the term of this patent subsequent to Oct. 27, 2009, has been disclaimed.

[21] Appl. No.: 679,075

[22] PCT Filed: Dec. 15, 1989

[86] PCT No.: PCT/EP89/01548

§ 371 Date: Aug. 23, 1991

§ 102(e) Date: Aug. 23, 1991

[87] PCT Pub. No.: WO90/07485

PCT Pub. Date: Jul. 12, 1990

[30] Foreign Application Priority Data

Dec. 24, 1988 [DE] Germany .......................... 38 43 930.1

[51] Int. Cl.$^6$ .................................................. C07C 69/52

[52] U.S. Cl. .................................................. 560/224
[58] Field of Search ............................................. 560/224

[56] References Cited

U.S. PATENT DOCUMENTS

| | | | |
|---|---|---|---|
| 4,053,504 | 10/1977 | Rosenkranz et al. | 560/4 |
| 5,053,316 | 10/1991 | Suzuki et al. | 430/281 |
| 5,159,106 | 10/1992 | Ritter et al. | 560/224 |

*Primary Examiner*—Gary L. Geist
*Assistant Examiner*—Rosalynd Williams
*Attorney, Agent, or Firm*—Wayne C. Jaeschke; John E. Drach; Henry E. Millson, Jr.

[57] ABSTRACT

The invention relates to a process for the production of (meth)acrylic acid esters of polyhydric alcohols by reaction of the reactants with acrylic acid and/or methacrylic acid in the presence of acidic esterification catalysts with addition of sterically hindered phenolic compounds as polymerization inhibitors. The process is characterized in that tocopherols are used as the sterically hindered phenolic compounds and α-tocopherol is preferably at least partly used. The process is preferably carried out using reaction mixtures which are liquid at room temperature and which are at least substantially free from solvents and/or azeotropic entraining agents; more particularly, the water of condensation formed is removed from the gas phase of the reaction zone.

21 Claims, No Drawings

PROCESS FOR PRODUCING ESTERS OF (METH) ACRYLIC ACID AND POLYHYDRIC ALCOHOLS

This invention relates to a process for the production of polyfunctional esters of acrylic acid and/or methacrylic acid—hereinafter referred to as (meth)acrylic acid esters or poly(meth)acrylic acid esters—with polyhydric alcohols by reaction of the reactants in the presence of acidic esterification catalysts with addition of polymerization inhibitors to the reaction mixture.

(Meth)acrylic acid esters of polyhydric alcohols, particularly from the group of dihydric to tetrahydric aliphatic saturated alcohols and their alkoxylation products, are being used to an increasing extent as highly reactive constituents in radiation-curing systems. Polyfunctional (meth)acrylic acid esters of the type in question may be used, for example, as paint constituents for hardening by electron beams or as a constituent of UV-hardening printing inks or corresponding paints, surfacing, molding or encapsulating compounds or even in adhesives, particularly anaerobic adhesives. However, their production is not without problems. The end products are required in particular to be colorless with a low acid value, high stability in storage and hardly any odor. (Meth)acrylic acid esters of the type in question generally cannot be purified by distillation on account of their high molecular weight and their high reactivity. Accordingly, the products are intended to accumulate directly as colorless products of the esterification reaction. The esterification reaction requires the presence of highly effective inhibitors which, in turn, should not initiate any unwanted secondary reactions, for example in the form of discoloration.

Extensive literature is available on the production of such polyfunctional (meth)acrylic acid esters of polyhydric alcohols, cf. in particular DE-OS 29 13 218 and the relevant literature cited therein. Thus, it is known from DE-AS 12 67 547 and from the Journal "Chem. and Ind." 18 (1970), 597, that polyfunctional (meth)acrylic acid esters can be produced by azeotropic esterification of (meth)acrylic acid with polyhydric alcohols in the presence of azeotropic entraining agents and also acidic catalysts and polymerization inhibitors, such as phenols, phenol derivatives, copper, copper compounds or phenothiazine. Organic or inorganic acids or acidic ion exchangers are used as the acidic catalysts, p-toluene sulfonic acid and sulfuric acid being preferred. The esterification reaction takes place in particular at temperatures in the range from 40° to 120° C. Suitable azeotropic entraining agents for removing the water of reaction are aliphatic or cycloaliphatic or aromatic hydrocarbons or mixtures thereof having boiling ranges within the stated temperature limits.

It is proposed in DE-OS 29 13 218 cited above to carry out the azeotropic esterification in the presence of at least one organic ester of phosphorous acid in addition to a phenol-based inhibitor. However, the reaction again has to be carried out in the presence of at least one aliphatic, cycloaliphatic and/or aromatic hydrocarbon boiling at 40° to 120° C. The water of reaction formed is said to be azeotropically removed from the reactor by this entraining agent. According to the Examples of this publication, the reaction time is put at 10 to 18 hours.

The problem addressed by the invention is to establish reaction conditions for the esterification reaction in question which, on the one hand, enable the reaction time to be considerably shortened but which, on the other hand, do not adversely affect the quality of the esterification products formed, particularly their high color quality. In addition, the invention seeks to eliminate the need for comparatively complex inhibitor systems of the type described in DE-OS 29 13 218 cited above. Another problem addressed by the invention is to enable the application inhibitor required in practice for the highly reactive systems in question to be used simultaneously as a reaction inhibitor in the synthesis of the polyfunctional (meth)acrylic acid esters.

The technical solution to the problems addressed by the invention is based inter alia on the observation that esterification products of comparatively high purity can be directly obtained as end products of the process, even in the absence of diluents or azeotropic entraining agents, and that it is even possible under the solventless reaction conditions to apply comparatively relatively drastic esterification conditions which enable the reaction time to be considerably shortened. To this end, it is necessary in particular to select the right polymerization inhibitor and to carry out the process under the conditions described hereinafter.

Accordingly, the present invention relates to a process for the production of (meth)acrylic acid esters of polyhydric alcohols by reaction thereof with acrylic acid and/or methacrylic acid in the presence of acidic esterification catalysts with addition of sterically hindered phenolic compounds as polymerization inhibitors. The new process is characterized in that tocopherols are used as the sterically hindered phenolic compounds and $\alpha$-tocopherols are at least partly used.

Tocopherols have occasionally been proposed as polymerization inhibitors in the literature. However, they have never been used as such in practice. Instead, this class of compounds is used for totally different applications as vitamin E. The invention is based on the surprising observation that the particular difficulties associated with the problem stated at the beginning can actually be effectively resolved by the use of tocopherols, particularly $\alpha$-tocopherol. It has in fact been found that, where these inhibitors are used, it is possible to apply drastic process conditions hitherto regarded as unuseable. Thus, in one preferred embodiment of the invention, the reaction mixtures used are liquid at room temperature and are at least substantially free from solvents and/or azeotropic entraining agents. It is particularly preferred to carry out the process in the complete absence of such liquid auxiliaries. In another preferred embodiment of the process according to the invention, the water of condensation formed during the esterification reaction is best removed from the gas phase of the reaction zone.

In another preferred embodiment of the invention, the reaction zone is purged with a gas stream and the gas stream in question is used in particular to remove the water of condensation formed during the esterification reaction from the reactor. It is preferred to use a gas stream which contains a limited amount of free oxygen. Depending on the particular process conditions selected, air or an oxygen-depleted gas mixture, for example a nitrogen/air mixture, may be used as the gas stream. In general, however, a certain content of free oxygen will be desirable in this gas phase delivered to the reaction mixture. These limited quantities of oxygen activate the inhibitor in known manner during the course of the reaction.

The oxygen content of the gas mixture is generally at least of the order of 1% by volume and preferably in the range from about 2 to 20% by volume. In the interests of reaction safety, the free oxygen contents are preferably in the lower half of this range, i.e. up to about 10% by volume and preferably up to about 7% by volume. In one preferred embodiment of the invention, the gas stream is fed into the liquid reaction mixture and can bubble through it, for example in finely divided form. It is best to use limited quantities of this gas stream so that there is no undesirably high discharge of reaction components, particularly the comparatively low-volatility acids.

The polymerization inhibitor or, optionally, the inhibitor mixture is typically added to the reaction mixture in quantities of from 200 to 10,000 ppm and preferably in quantities of from about 300 to 2000 ppm, based in each case on the weight of the reaction mixture of (meth)acrylic acid and polyhydric alcohols.

Suitable polyalcohols for esterification are, for example, ethylene glycol, propylene glycol, butane-1,4-diol, hexane-1,6-diol, neopentyl glycol, diethylene glycol, triethylene glycol, dimethylol propane, glycerol, trimethylol propane, trimethylol hexane, trimethylol ethane, hexane-1,3,5-triol and pentaerythritol. According to the invention, however, particularly suitable polyhydric alcohols are also the alkoxylation products of the above-mentioned polyhydric alcohols, particular significance being attributed in this regard to the ethoxylation products and/or propoxylation products. Chain-extended polyhydric alcohols of this type may contain considerable quantities of polyalkoxide groups, for example 1 to 50 mol and preferably about 1 to 20 mol ethylene oxide per g-equivalent hydroxyl groups.

Suitable esterification catalysts for the process according to the invention are commercially available organic or inorganic acids or even acidic ion exchangers, particular significance being attributed to the corresponding compounds frequently used in practice, namely p-toluene sulfonic acid and sulfuric acid. The esterification catalyst is used in quantities of, for example, from 0.1 to 5% by weight, based on the esterification mixture.

The reactants are preferably reacted at sump temperatures of at least about 90° C. and, preferably, of at least about 100° C., the temperature range up to about 150° C. being particularly suitable. The reaction may be carried out under normal pressure, although it is best carried out under reduced pressure. Where the reaction is carried out under reduced pressure, it is possible in one particular embodiment to reduce the pressure towards lower pressures either in steps or continuously.

Through the possibility of working under comparatively drastic esterification conditions and, at the same time, reduced pressure, the reaction time is considerably shortened by comparison with hitherto known processes. Thus, yields of at least 90% of the theoretical and, preferably, of at least around 94% of the theoretical may be obtained in the process according to the invention for a reaction time of no more than about 10 hours and, preferably, of no more than about 8 hours at temperatures in the range from about 100° to 140° C. Nevertheless, the reaction products are obtained in the form of a stabilized mass which is light in color or may be effectively purified by a simple aftertreatment.

The crude reaction product containing the acidic esterification catalyst is subsequently subjected to neutralization. This neutralization step may be carried out under known wet conditions, for example by the use of aqueous solutions containing soda and, optionally, sodium chloride. In one preferred embodiment, however, the crude reaction product containing the acidic catalyst is subjected to dry neutralization. Suitable dry neutralizing agents are the oxides and/or hydroxides of the alkali metals, the alkaline earth metals and/or aluminium. Corresponding compounds of magnesium or calcium are particularly suitable for the dry neutralization.

(Meth)acrylic acid and the alcohols may be used in equivalent quantities for the esterification reaction. However, where more than dihydric alcohols are used, it is readily possible only partly to esterify the hydroxyl groups. For full esterification, it may be best to use the acid component in a slight excess over the stoichiometric quantity required for esterification of the hydroxyl groups. This slight excess may amount to at least about 10 mol-%. If desired, an inhibitor may be additionally incorporated in the reaction product on completion of the reaction.

Should slight discoloration of the reaction product occur after all during production under the drastic esterification conditions according to the invention, it may readily be eliminated by an aftertreatment with decolorizing agents. Aluminium oxide, for example, is a suitable decolorizing agent.

EXAMPLES

Example 1

324.0 g acrylic acid, 368.2 g of an ethoxylated trimethylol propane (OH value 680 mg KOH/g substance), 24.2 g p-toluene sulfonic acid and 1.38 g D,L-α-tocopherol (Merck, 2260 ppm, based on the quantity of product) were weighed into a 1 liter three-necked flask.

An air/nitrogen mixture (5% by volume $O_2$; 20 l/h) was passed through the reaction mixture during the esterification reaction and water was removed. For a constant bath temperature of 145° C. and a maximum sump temperature of 140° C., the esterification time was 4 hours.

Crude product data:
Acid value: 20.3 mg KOH/g
OH value: 19.7 mg KOH/g
Yield: 95.0%
Gardner color standard number: 7–8
$H_2O$ content: 0.12%

The crude product was washed with 700 ml 10% by weight aqueous sodium carbonate solution, dried in vacuo for 3 hours at 80° C./40 mbar and then filtered.
Product data:
Acid value: <1 mg KOH/g
OH value: 43 mg KOH/g
Gardner color standard number: 3–4
$H_2O$ content: 0.31%

Example 2

324.0 g acrylic acid, 368.2 g of an ethoxylated trimethylol propane (OH value 680 mg KOH/g substance) and. 24.2 g p-toluene sulfonic acid were weighed into a 1 liter flask and inhibited with 1.22 g α-tocopherol (HENKEL RGaA, Duesseldorf, Germany, 2000 ppm, based on the quantity of product).

An air/nitrogen mixture (5% by volume $O_2$; 40 l/h) was passed through the reaction mixture during the esterification reaction and water was removed. For a constant bath temperature of 125° C., a maximum sump temperature of 120° C. and a pressure of 700 mbar, the esterification time was 4 hours.

Crude product data:
Acid value: 17.0 mg KOH/g
OH value: 33.6 mg KOH/g
Yield: 91.4%
Gardner color standard number: 7–8
$H_2O$ content: 0.16%

The crude product was washed with 1400 g aqueous 16% by weight NaCl/4% by weight NaHCO$_3$ solution, dried in vacuo for 2 hours at 80° C./40 mbar and then filtered.
Product data:
Acid value: <1 mg KOH/g
OH value: 43 mg KOH/g
Gardner color standard number: 5–6
H$_2$O content: 0.42%.

Example 3

The procedure was as in Example 2, except that 5000 ppm of a mixed tocopherol (HENKEL) were used instead of the 2000 ppm α-tocopherol.
Crude product data:
Acid value: 33.1 mg KOH/g
OH value: 27.8 mg KOH/g
Yield: 92.9%
Gardner color standard number: 12
H$_2$O content: 0.18%
The crude product was worked up as in Example 1.
Product data:
Acid value: <1 mg KOH/g
OH value: 39 mg KOH/g
Gardner color standard number: 5–6
H$_2$O content: 0.25%.

Example 4

1559.5 g acrylic acid, 1521.0 g of an ethoxylated trimethylol propane (OH value 665 mg KOH/g substance) and 107.8 g p-toluene sulfonic acid were weighed into a 3-liter reactor and inhibited with 4.12 g α-tocopherol (HENKEL, 1650 ppm, based on the quantity of product). Air (40 l/h) was passed through the reaction mixture during the esterification reaction and the excess acrylic acid was removed. For a maximum sump temperature of 105° C. and a pressure of 400 mbar, the esterification time was 6 hours.
Crude product data:
Acid value: 24.9 mg KOH/g
OH value: 23.5 mg KOH/g
Yield: 93.9%
Gardner color standard number: 11
H$_2$O content: 0.25%
The crude product was neutralized by addition of 102.1 g solid Ca(OH)$_2$ and stirring for 1.5 hours at 80° C./50 mbar.
Product data:
Acid value: <1 mg KOH/g
OH value: 26.5 mg KOH/g
Gardner color standard number: 3–4
H$_2$O content: 0.18%

TABLE 1

| Bulk esterification with vitamin E as inhibitor | | | | |
|---|---|---|---|---|
| Inhibitor/ | Reaction conditions | | Gardner color | Yield |
| quantity ppm | T °C. | p mbar | standard number of the product | *1 % |
| DL-a-tocopherol (Merck) | | | | |
| 5000 | 140 | 1013 | 5–6 | *2 93.8 |
| 2260 | 140 | 1013 | 3–4 | *3 95.0 |
| α-Tocopherol (Henkel) | | | | |
| 10000 | 140 | 1013 | 7–8 | *3 93.1 |
| 5000 | 120 | 700 | 7–8 | *2 92.5 |
| 2000 | 120 | 700 | 5–6 | *2 91.4 |
| 1650 | 105 | 400 | 3–4 | *4 93.9 |
| 1000 | 105 | 400 | 4–5 | *4 92.5 |
| 500 | 105 | 400 | 4–5 | *4 93.3 |
| 300 | 105 | 400 | 3–4 | *4 93.1 |
| Mixed tocopherol (Henkel) | | | | |
| 10000 | 140 | 1013 | 9–10 | *2 91.3 |
| 5000 | 120 | 700 | 5–6 | *3 92.9 |
| 2000 | 120 | 700 | 5–6 | *3 93.8 |

*1 Yield, based on OH value
*2 Crude product washed with 4% by weight sodium hydrogen carbonate/16% by weight sodium chloride, aqueous solution, and subsequently dried
*3 Crude product washed with 10% by weight sodium carbonate solution and subsequently dried
*4 Crude product neutralized with solid calcium hydroxide (2-fold equimolar excess, based on the acid value)

Example 5

1559.5 g acrylic acid, 1521.0 g of an ethoxylated trimethylol propane (OH value 665 mg KOH/g substance) and 107.8 g p-toluene sulfonic acid were weighed into a 3-liter reactor and inhibited with 4.99 g α-tocopherol (HENKEL, 2000 ppm, based on the quantity of product). Air (40 l/h) was passed through the reaction mixture during the esterification reaction and the excess acrylic acid and water were removed. For a sump temperature of 105° C. and a pressure of 400 mbar, the esterification time was 6 hours.
Crude product data:
Acid value: 26.3 mg KOH/g
OH value: 24.8 mg KOH/g
Yield: 94.2%
Gardner color standard number: 10
H$_2$O content: 0.18%
The crude product was neutralized by addition of 107.8 g solid Ca(OH)$_2$ and stirring for 1.5 hours at 80° C./50 mbar and then filtered in a pressure nutsche.
Product data:
Acid value: <1 mg KOH/g
OH value: 27.0 mg KOH/g
Gardner color standard number: 3–4
H$_2$O content: 0.17%
To improve its color, the product was stirred for 2 hours at 80° C. with 240 g Al$_2$O$_3$ (basic) and then filtered in a pressure nutsche.
Acid value: <1 mg KOH/g
OH value: 28.0 mg KOH/g
Gardner color standard number: <1

Example 6

1320.0 g acrylic acid, 1861.7 g of a propoxylated neopentyl glycol (OH value 460 mg KOH/g substance) and 111.4 g p-toluene sulfonic acid were weighed into a 3-liter reactor and inhibited with 5.37 g α-tocopherol (HENKEL, 2000 ppm, based on the quantity of product). Air (40 l/h)

was passed through the reaction mixture during the esterification reaction and the excess acrylic acid and water were removed. For a sump temperature of 105° C. and a pressure of 400 mbar, the esterification time was 6 hours.

Crude product data:
Acid value: 31.0 mg KOH/g
OH value: 18.0 mg KOH/g
Yield: 94.6%
Gardner color standard number: 8
$H_2O$ content: 0.21%

The crude product was neutralized by addition of 114 g solid $Ca(OH)_2$ and stirring for 2 hours at 80° C./50mbar and then neutralized in a pressure nutsche.

Product data:
Acid value: <1 mg KOH/g
OH value: 21.0 mg KOH/g
Gardner color standard number: 3
$H_2O$ content: 0.17%

To improve its color, the product was stirred for 2 hours at 80° C. with 260 g $Al_2O_3$ (basic) and then filtered in a pressure nutsche.
Acid value: <1 mg KOH/g
OH value: 21.0 mg KOH/g
Gardner color standard number: <1

TABLE 2

Decolorizing effect of $Al_2O_3$ (basic) in bulk esterification with vitamin E as inhibitor

| Quantity of $Al_2O_3$ % by weight, based on quantity of product | Gardner color standard number |
|---|---|
| Trimethylol propane + 3 EO triacrylate/Gardner color standard number before purification 3–4 | |
| 5 | 2–3 |
| 10 | 1 |
| 15 | <1 |
| 20 | <1 |
| Neopentyl glycol + 2 PO diacrylate/Gardner color standard number before purification 3 | |
| 5 | 2 |
| 10 | 1 |
| 15 | <1 |
| 20 | <1 |

We claim:

1. In a process for the production of (meth)acrylic acid esters of polyhydric alcohols by reaction of at least one polyhydric alcohol with acrylic acid and/or methacrylic acid in the presence of an acidic esterification catalyst and a polymerization inhibitor comprising a sterically hindered phenolic compound, the improvement wherein the polymerization inhibitor consists of at least one tocopherol.

2. The process of claim 1 wherein the at least one tocopherol is α-tocopherol.

3. The process of claim 1 wherein the reaction zone is purged with a gas stream containing free oxygen.

4. The process of claim 3 wherein air or a nitrogen/air mixture is used as the gas stream.

5. The process of claim 1 wherein the water of condensation formed in the process is removed from the gas phase of the reaction zone.

6. The process of claim 1 wherein the reaction is carried out at a sump temperature in the range of from about 90° to about 150° C.

7. The process of claim 6 wherein said temperature is from about 100° to about 140° C.

8. The process of claim 1 wherein the reaction is carried out at subatmospheric pressure.

9. The process of claim 1 wherein the at least one tocopherol is present in from about 200 to about 10,000 ppm, based on the weight of the reaction mixture.

10. The process of claim 9 wherein from about 300 to about 2,000 ppm of phenolic compound is present.

11. The process of claim 1 wherein the reaction is carried out to a yield of product of at least 90% based on theoretical, and wherein the reaction time is not greater than about 10 hours.

12. The process of claim 1 wherein the reaction product is subjected to dry neutralization.

13. The process of claim 12 wherein the dry neutralization is carried out with at least one oxide or hydroxide of an alkali metal, an alkaline earth metal, or aluminum.

14. The process of claim 1 wherein the reaction product is treated with a decolorizing agent.

15. In a process for the production of (meth)acrylic acid esters of polyhydric alcohols by reaction of at least one polyhydric alcohol with acrylic acid and/or methacrylic acid in the presence of an acidic esterification catalyst and a sterically hindered phenolic compound as a polymerization inhibitor, the improvement wherein at least one tocopherol is used as the sterically hindered phenolic compound, and the reaction mixture is liquid at room temperature and is at least substantially free from solvents and azeotropic entraining agents.

16. The process of claim 15 wherein, the reaction zone is purged with a gas stream containing free oxygen, and the water of condensation formed in the process is removed from the reaction zone.

17. The process of claim 16 wherein the reaction is carried out at a sump temperature in the range of from about 90° to about 150° C.

18. The process of claim 17 wherein the temperature is in the range of from about 100° to about 140° C.

19. The process of claim 16 wherein the reaction is carried out at subatmospheric pressure.

20. The process of claim 16 wherein from about 300 to about 2000 ppm of phenolic compound is present.

21. The process of claim 16 wherein the reaction is carried out to a yield of product of at least 90% based on theoretical, the reaction time is not greater than about 10 hours, and the reaction product is subjected to dry neutralization.

* * * * *